(12) United States Patent
Soong et al.

(10) Patent No.: US 7,250,615 B1
(45) Date of Patent: Jul. 31, 2007

(54) PORTABLE SANITIZATION SYSTEM AND METHOD

(76) Inventors: A. Joseph Soong, 412 N. Bushnell Ave., #F, Alhambra, CA (US) 91801; James W. Soong, 521 Susana Ave., Redondo Beach, CA (US) 90277

( * ) Notice: Subject to any disclaimer, the term of this patent is extended or adjusted under 35 U.S.C. 154(b) by 184 days.

(21) Appl. No.: 10/962,891

(22) Filed: Oct. 12, 2004

Related U.S. Application Data

(63) Continuation of application No. 10/836,151, filed on Apr. 30, 2004, now abandoned.

(51) Int. Cl.
*A61L 2/08* (2006.01)

(52) U.S. Cl. .................. 250/492.1; 250/493.1; 422/22

(58) Field of Classification Search ............. 250/492.1, 250/492.3, 493.1; 422/4, 22, 121, 122, 186.05; 435/4, 6, 91.2; 424/9.361
See application file for complete search history.

(56) References Cited

U.S. PATENT DOCUMENTS 6,822,250 B2 * 11/2004 Korenev .................. 250/492.3

* cited by examiner

*Primary Examiner*—Kiet T. Nguyen

(57) ABSTRACT

A selector receives inputs of a user. An energy generator produces energy to neutralize environmental danger. A controller, communicatively coupled with the selector, controls operation of the energy generator based on the inputs. A case, containing the energy generator and the controller, is dimensioned to fit in the hand of the user.

20 Claims, 15 Drawing Sheets

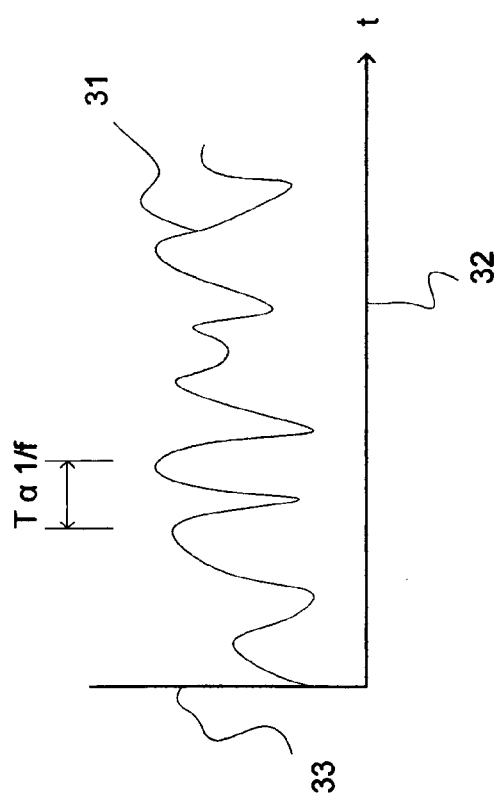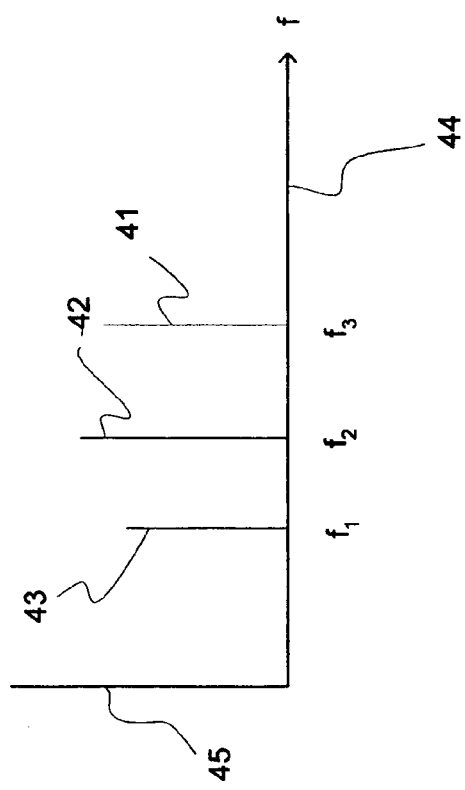

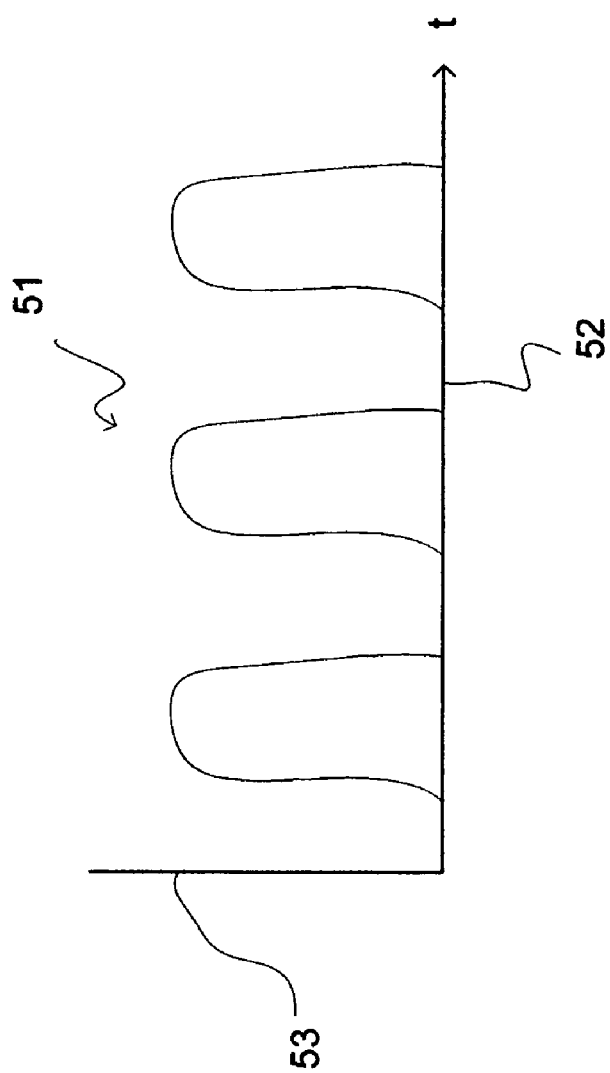

PORTABLE SANITIZATION SYSTEM AND METHOD

This application is a continuation of application Ser. No. 10/836,151, filed Apr. 30, 2004 now abandoned, entitled "Portable Sanitization System and Method", and naming A. Joseph Soong and James W Soong as inventors application Ser. No. 10/836,151 is hereby incorporated by reference in its entirety and for all purposes.

FIELD OF THE INVENTION

The present invention relates to portable sanitization systems and methods and, more specifically, to handheld energy delivery to address various environment pathogens.

BACKGROUND

Germs, bacteria, and viruses that have the potential enter or otherwise affect the human body can cause great risk and harm to human health and well-being. Such pathogens have threatened human health by their appearance on food, hands, and other items that can come in contact with the body. Once present in the human body the pathogens are capable of causing illness and in some circumstances even worse consequences.

According to the Centers for Disease Control, irradiation is a safe technology that can eliminate disease-causing germs from foods. Like pasteurization of milk and pressure cooking of canned foods, treating food with ionizing radiation can kill bacteria and parasites that would otherwise cause foodborne disease. The food that space astronauts eat has been sterilized by irradiation to avoid getting foodborne illness in space. The effects of irradiation on the food and on animals and people eating irradiated food have been studied extensively. Although their conclusions and findings have changed, these studies show effective cleansing results when certain irradiation is used on foods. Similar technology is used in industrial settings to sterilize medical devices so they can be used in surgery or implanted without risk of infection.

BRIEF DESCRIPTION OF THE DRAWINGS

FIG. 3 shows an energy form representing delivered energy in accordance with one of many embodiments of the present invention;

FIG. 4 shows energy forms representing delivered energy in accordance with one of many embodiments of the present invention;

FIG. 5 shows a graph of delivered energy in accordance with one of many embodiments of the present invention;

DETAILED DESCRIPTION

Figure 1:
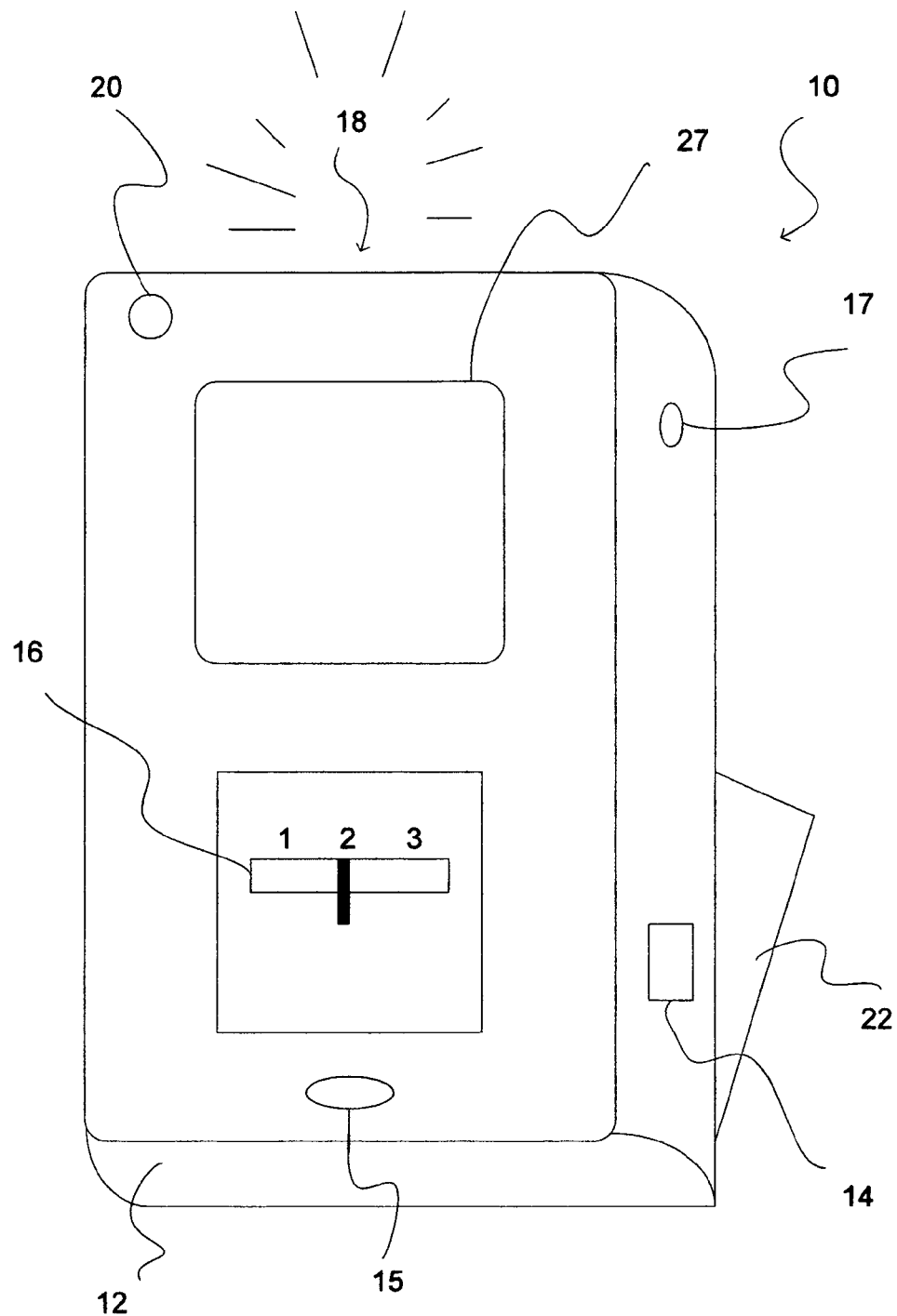
FIG. 1 shows a handheld sanitizer in accordance with one of many embodiments of the present invention.

FIG. 1 illustrates a handheld sanitizer 10 in accordance with portable sanitization systems and methods of the present invention. The handheld sanitizer 10 can be conveniently held in and controlled by a hand of a person possessing the handheld sanitizer 10. The handheld sanitizer 10 can be used by a person or persons to degrade, reduce, or destroy harmful organisms that would otherwise endanger the health and well being of the person or others. The handheld sanitizer 10 can be employed to, for example, sterilize, cleanse, and disinfect objects and materials of the user, nearby persons, or of the user's surroundings such as food, utensils, clothing, hands, objects to be handled or ingested, or any other item that might contain or transmit potential harm.

The handheld sanitizer 10 includes a case 12, a switch 14, a selector 16, a trigger 17, a director 18, an indicator 20, and a door 22. In one embodiment of the present invention, the case 12 forms an outer surface of the handheld sanitizer 10. The case 12 is dimensioned to easily fit in the grip or hand of a person. The case 12 is of a durable and rigid nature sufficient to withstand ordinary consumer use and handling. The case 12 can take any shape. In one embodiment of the present invention, the case 12 is optimally contoured to fit comfortably and controllably in the hand of a person. The case 12 can be influenced by the layout and design of underlying components inside the case 12, as will be discussed in more detail below. The case 12 can be made of a material that is optimized to be resistant or immune to pathogens. In one embodiment, the case 12 can be removable, disposable, and replaceable to help optimize the cleanliness of the handheld sanitizer 10. In use, a user may choose to wear sanitary or clean gloves to handle the handheld sanitizer 10.

The case 12 exposes the switch 14. The switch 14 allows a user of the handheld sanitizer 10 to turn the handheld sanitizer 10 on and off. The switch 14 can be a mechanism that slides between on and off positions. In other embodiments of the present invention, the switch 14 can be of a push button nature or other switch variety.

The case exposes the trigger 17. After the handheld sanitizer 10 is turned on using the switch 14, the delivery of energy is initiated by appropriate depression or other engagement of the trigger 17. A first depression of the trigger 17 initiates delivery of energy while a second depression of the trigger 17 ends delivery of energy.

The case 12 exposes the selector 16. The selector 16 allows a user to choose particular settings affecting operation of the handheld sanitizer 10. In one embodiment of the present invention, the selector 16 is a mechanical sliding switch that includes three possible selection settings. The selection settings correspond to three objects to be energized. Of course, many other selection settings in any number are possible in alternate embodiments of present invention. For example, the settings could instead correspond to high, medium, or low power or frequency settings. As yet another example, the selector 16 could have 5 settings instead of three and, under this example, correspond to attributes other than food items and power and frequency levels. Alternate embodiments of the selector 16 are discussed in more detail below.

The handheld sanitizer 10 includes the director 18 to emit energy. In one embodiment of the present invention, the director 18 can be an exposed antenna for radiating electromagnetic energy. In another embodiment of the present invention, the director 18 can be an electrode for delivering electrical energy. In yet another embodiment, the director 18 can be an electron gun apparatus to propel high energy electrons in an electron beam. It will be appreciated that the director 18 can be any other kind of device to suitably deliver a particular kind of energy to be applied by the handheld sanitizer 10.

The case 12 exposes the indicator 20. The indicator 20 indicates when the handheld sanitizer 10 is active and delivering energy. The indicator 20 serves as a signal to the user and others that the handheld sanitizer 10 is in use. In one embodiment of the present invention, the indicator 20 is an LED.

The handheld sanitizer 10 includes the door 22 to allow access to the components inside the handheld sanitizer 10. The door 22 allows maintenance and repair to be performed on the handheld sanitizer 10.

Figure 2:
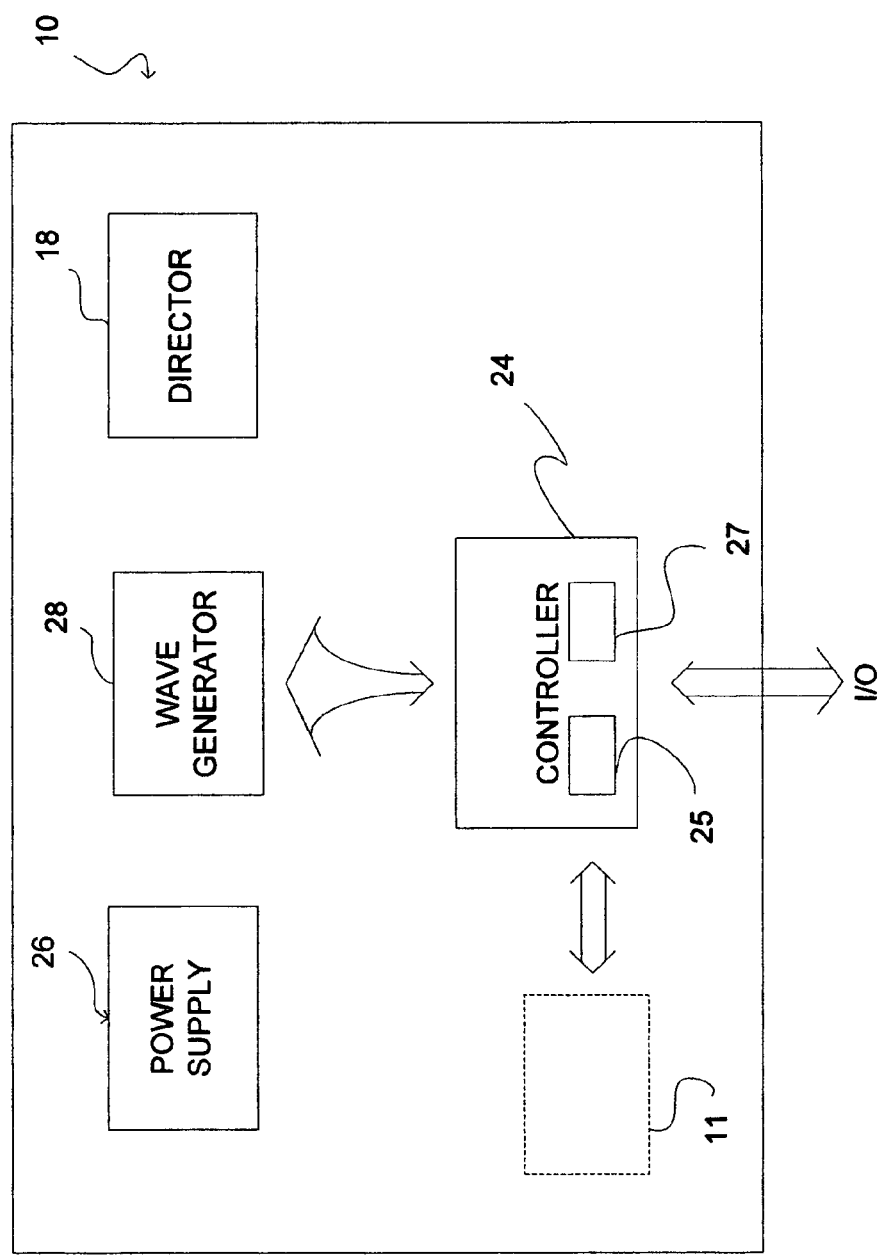
FIG. 2 shows components of the handheld sanitizer in accordance with one of many embodiments of the present invention.

FIG. 2 illustrates a simplified, logical block diagram of functional, but not necessarily physical, components of the handheld sanitizer 10. In one embodiment of the present invention, the handheld sanitizer 10 includes a controller 24, power supply 26, a energy generator 28, the director 18, and the indicator 20. The controller 24 is communicatively linked with the switch 14, the selector 16, and the trigger 17. The controller 24 receives user commands as inputs from the switch 14, the selector 16, and the trigger 17. The controller 24 includes a dock 25 and a memory 27, and is programmed with information to control the handheld sanitizer 10 based on selectable settings of the selector 16 and other considerations such as safety, as will be discussed in more detail below. Based on the inputs, the controller 24 sends and receives signals to and from the indicator 20, the power supply 26, energy generator 28, and the director 18 to control the operation of the handheld sanitizer 10 in accordance with user programming and commands. The controller can activate and shut down the generation and emission of energy. The power supply 26 powers the indicator 20 and the energy generator 28. The power supply can be of many varieties including but not limited to plug-in and rechargeable types. Further, the handheld sanitizer 10 can have solar panels that allow solar energy to power the handheld sanitizer 10. The energy generator 28 generates energy or signals that are provided to the director 18. The director 18 in turn emits energy to direct at environmental dangers.

In other embodiments of the present invention, the functional components of the handheld sanitizer 10 could be physically integrated. For example, the power supply 26 and energy generator 28 could be unified into one component. In addition, the handheld sanitizer 10 could include additional components not illustrated or discussed herein. For example, an amplifier could be included between the power supply 26 and the energy generator 28, or elsewhere. As yet another example, the power supply 26, the energy generator 28, and the director 18 could be integrated into one component that is controlled by the controller 24 to generate and apply energy. As still another example, the memory 27 could be separate from the controller 24. It will be appreciated by those of ordinary skill in the art that the design of the parts of the handheld sanitizer 10 could be distributed over many functional or physical components, or integrated into fewer or even one functional or physical component in accordance with the present invention, such components not necessarily described or illustrated herein. Further, the internal parts of the handheld sanitizer 10 could be distributed over many or various functional or physical components not shown in FIG. 2 but still in accordance with the present invention.

FIG. 3 is a graphical illustration of an exemplary energy form 31 of electromagnetic energy generated from the director 18 to destroy environment danger. The energy form 31 is plotted over an x-axis 32 representing time and a y-axis representing amplitude. The distance between peaks (or valleys) is indicative of the frequency of the energy form 31. The energy form 31 produced by the handheld sanitizer 10 is of a nature sufficient to degrade, reduce, or destroy some, but perhaps not all, environmental danger. The energy form produced by the handheld sanitizer 10 in accordance with the present invention, while capable of at least degrading environmental danger, is safe for the user of the handheld sanitizer 10 and others adjacent the user.

FIG. 4 is a graphical illustration of other exemplary energy forms 41-43 capable of being produced by the handheld sanitizer 10 and transmitted by the director 18. The energy forms 4143 are plotted over an x-axis 44 representing frequency and a y-axis 45 representing amplitude.

The forms of energy depicted in FIGS. 3 and 4 are exemplary only. Other forms of energy generated by the handheld sanitizer 10 to safely and effectively address environmental danger are contemplated in accordance with the present invention and not necessarily best represented in the graphical format of FIGS. 3 and 4.

The director 18 can transmit various forms of energy in accordance with the present invention. For example, the director 18 can transmit UV radiation, gamma rays, x-rays, electron beams, radio frequency waves, laser light, electrical current, electrostatic discharge, and other kinds of radiation and other energy. Certain kinds of energy, rightly or wrongly so, have been associated with effectively addressing certain kinds of environmental danger. For example, it has been widely held that the C bandwidth of UV radiation is effective in killing bacteria and viruses.

As another example, radioactive isotopes of cobalt or cesium, electron accelerators, or X-rays are three possible sources of radiation for cleansing food. These three exemplary sources are believed to produce similar effects against food pathogens and pests since they fall in the short-wave, high energy region of the frequency spectrum. The dose of radiation energy absorbed by, for example, food as it passes through a radiation field during cleansing is generally measured in Grays (G) or kiloGrays (kGy) where 1 Gray=0.001 kGy=1 joule of energy absorbed per kilogram of food irradiated. Dose can also be measured in Rads (100 Rads=1

Gray). The dose can be determinative of what environmental dangers are effectively addressed. For example, a "medium" dose (1–10 kGy) is believed to be capable of controlling *salmonella, shigella, campylobacter*, and *yersinia* in meat, poultry, and fish. It will be appreciated by those of ordinary skill in the art that there has been, still is, and likely will continue to be debate and disagreement over what kinds of energy, and in what amounts, is safe for humans. Similarly, there has been, still is, and likely will continue to be debate over what kinds of energy is capable of degrading, reducing, or destroying germs, viruses, bacteria, fungi, spores, mold, and other agents harmful to human health. The present invention is designed to employ and apply safe and effective kinds and levels of energy to address environmental dangers, no matter how opinions about safety and effectiveness may change over time. The energy produced by the handheld sanitizer 10 of the present invention can take many different forms not to be necessarily limited by earlier, current, or later thinking regarding what constitutes safe and effective kinds and levels of energy.

FIG. 5 is a graphical illustration of an exemplary application of a series of energy pulses 51. The pulses 51 are plotted over the x-axis 52 representing time and the y-axis 53 representing energy. The pulses 51 are applied by the director 18 to neutralize environmental danger. In one embodiment of the present invention, the director 18 is an electrode that directly applies pulses of electrostatic discharge or electrical current energy to the hand or other body parts to sterilize the hand or other body parts of the user or others by eliminating germs, bacteria, viruses, or other pathogens thereon. When electrostatic energy is emitted or discharged by the handheld sanitizer 10, the handheld sanitizer 10 may produce sparks when applied to a particular object. In other embodiments of the present invention, the pulses 15 are applied by the director 18 to address other environmental dangers. For example, the pulses 15 could be applied to food or other items for which sterilization would be useful. It will be appreciated that, in addition to electrostatic discharge and electrical current energy, other kinds of energy such as radiation, electromagnetic wave, and other kinds of potentially sanitizing energy can be emitted as energy pulses, rather than as continuous applications of energy, in accordance with the present invention.

Figure 6:
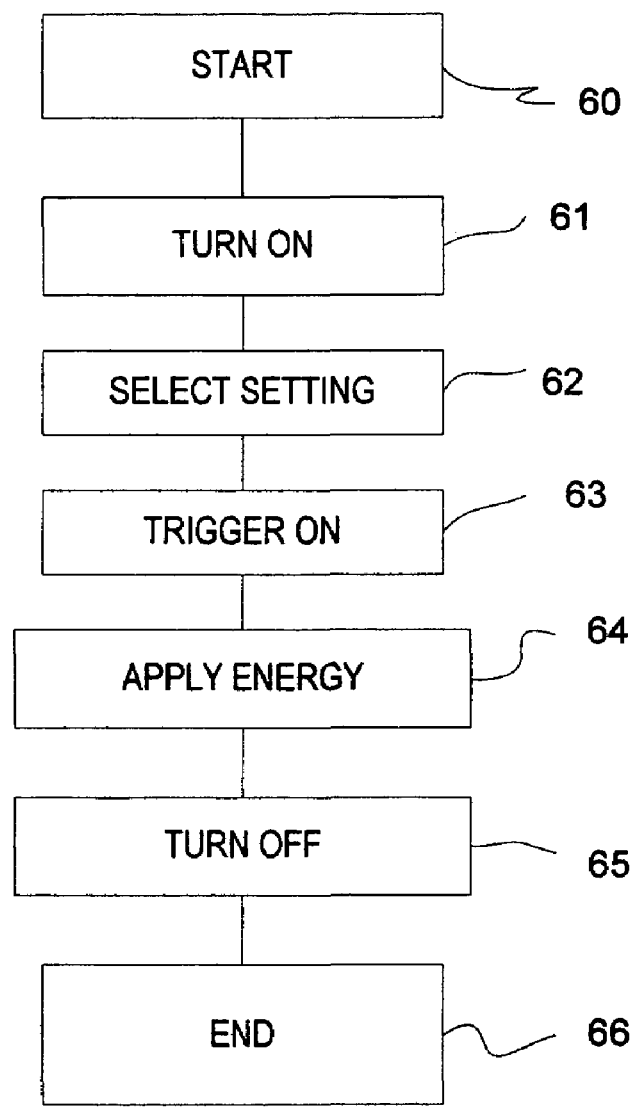
FIG. 6 shows a flow diagram of a method of using the handheld sanitizer in accordance with one of many embodiments of the present invention.

The depictions of energy in FIGS. 4-6, as plotted and graphed, are exemplary only. The precise graphical representation and characteristics of energy emitted by the handheld sanitizer 10 (such as wavelength, frequency, power, amplitude, duration, etc.) can take many alternative forms and can reflect any kinds of energy that are effective in addressing pathogens. In one embodiment of the present invention, the handheld sanitizer 10 can emit various energy forms.

FIG. 6 is a flow chart representing a method of applying energy to address environmental danger using the handheld sanitizer 10 in accordance with the present invention. At step 60 the method begins and proceeds to step 61 where the handheld sanitizer 10 is turned on by control of the switch 14. The method proceeds to step 62 where a particular setting of the selector 16 is selected. The method proceeds to step 63 where the trigger 17 is engaged. The method proceeds to a step 64 where energy generated by the handheld sanitizer 10 is directed by the director 18 to a desired target to address environmental danger. The method proceeds to step 65 where the handheld sanitizer 10 is turned off by control of the switch 14. The method proceeds to step 66 where the method ends.

Figure 7:
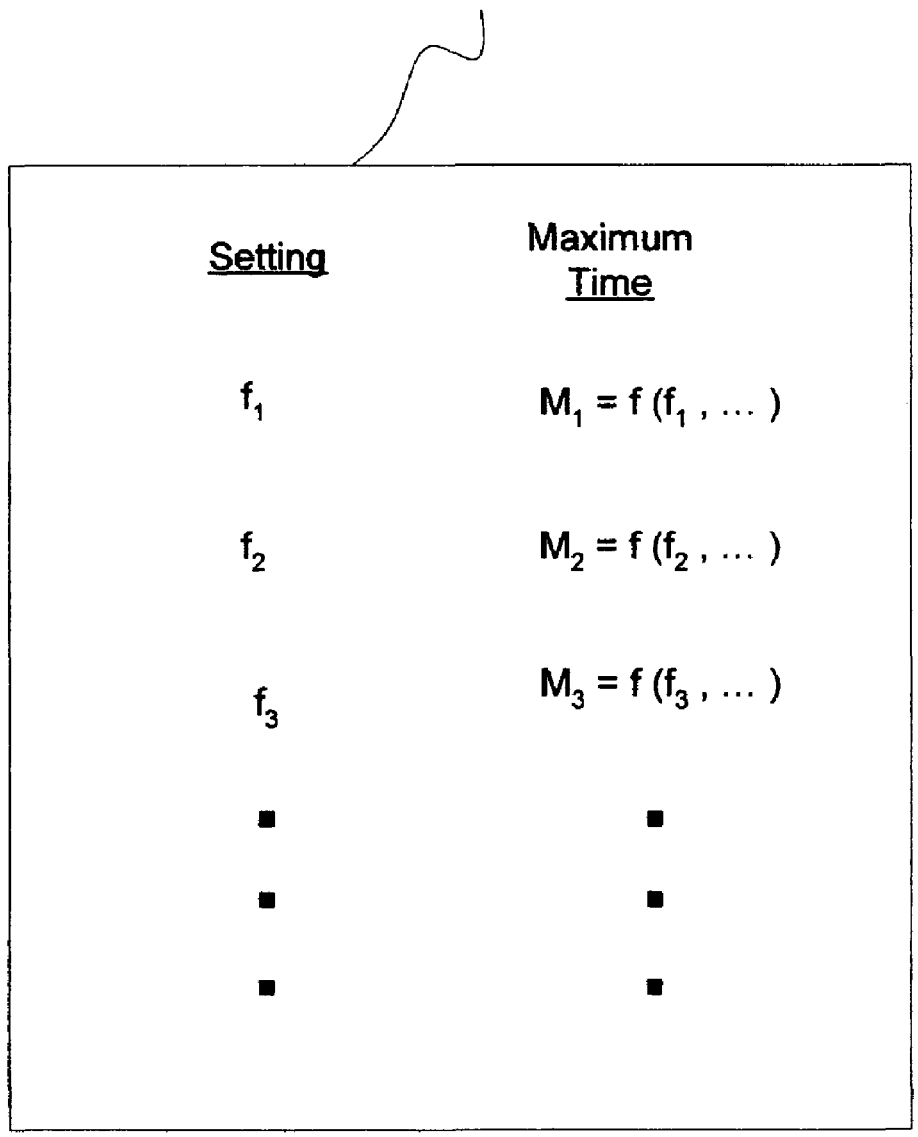
FIG. 7 shows a table listing settings and maximum times in accordance with one of many embodiments of the present invention.

FIG. 7 illustrates a table 70 that exemplarily lists settings based on the attribute of frequency fi of electromagnetic wave energy. Of course other settings based on other attributes are possible. The table 70 also exemplarily lists values of maximum time Mi that can be based on consideration of many factors including but not limited to effectiveness and safety. At a given frequency or power level setting of the selector 16, the application of energy to environmental danger should last in duration long enough to neutralize the danger but not long enough to cause harm to the user or any benign environmental objects within reach of the transmitted energy. The maximum time Mi is formulated in due consideration of these factors, with safety as a dominant factor. For example, when a setting corresponding to a particular frequency f1 is selected, the maximum time M1 is a function of the frequency f1 and other factors including but not limited to the particular kind of environmental danger, the proximity of benign environmental objects, and human sensitivity to the frequency f1. After the handheld sanitizer 10 is turned on at a particular setting fi, the handheld sanitizer 10 will automatically turn off after time Mi has passed. In one embodiment of the present invention, the table 70 is stored or programmed in the controller 24 or the memory 27. When the time Mi is reached during application of the handheld sanitizer 10, the controller 24 automatically provides a command to the power supply 26 or other components of the handheld sanitizer 10 to end application of energy. In one embodiment of the present invention, the maximum time M is preprogrammed into the handheld sanitizer 10. In one embodiment of the present invention, the maximum time M is stored in the memory 27. In one embodiment of the present invention, an operating system, BIOS, or other software can be stored in the memory 27, or a ROM, to allow operation of and interaction with the handheld sanitizer 10.

Figure 8:
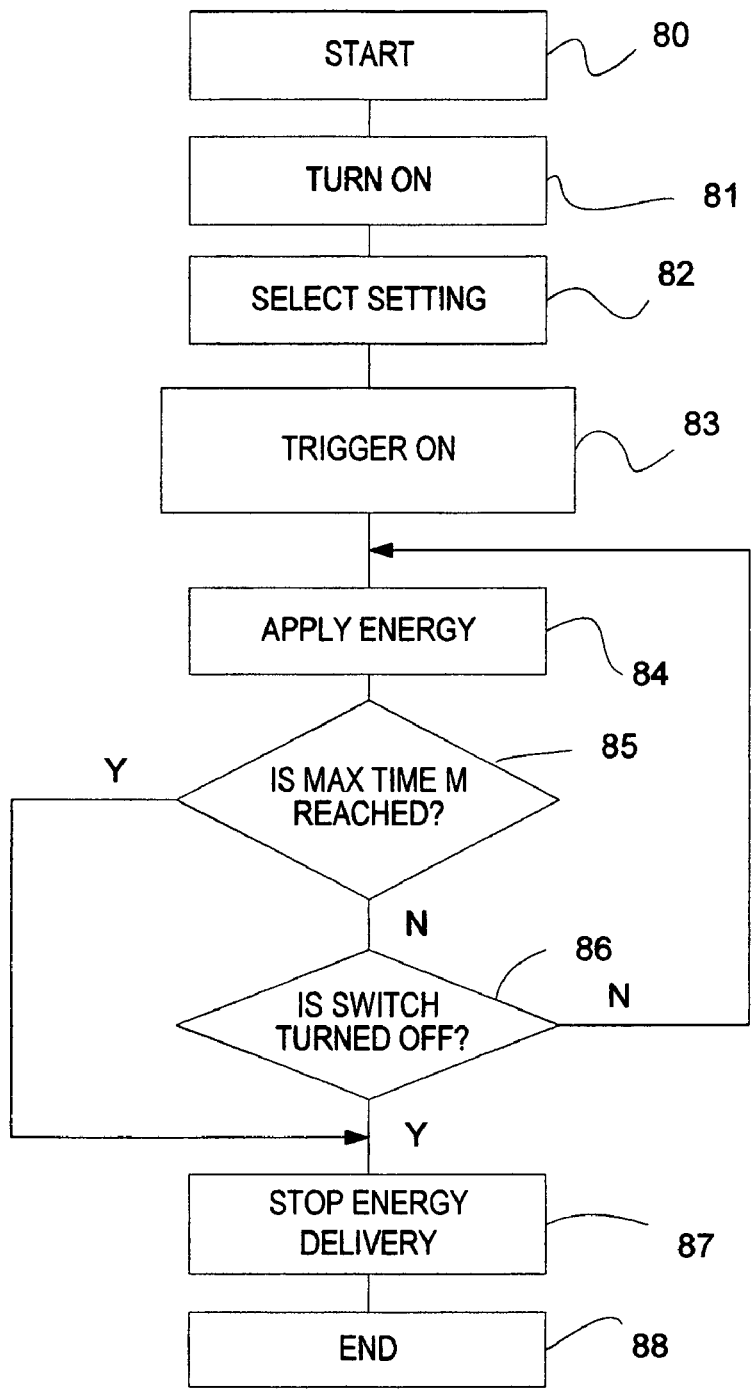
FIG. 8 shows a flow diagram of a method to provide automatic shutoff in accordance with one of many embodiments of the present invention.

FIG. 8 is a flow chart representing a method in accordance of the present invention to provide automatic shut off of the handheld sanitizer 10. At step 80 the method begins and proceeds to step 81 where the handheld sanitizer 10 is turned on by control of the switch 14. The method proceeds to step 82 where a setting of the selector 16 is selected. The method proceeds to step 83 where the trigger 17 is engaged. The method proceeds to step 84 where the handheld sanitizer 10 directs energy at the desired item. The method proceeds to decision step 85 where it is determined whether the maximum time M has been reached for the particular setting of the selector 16. If the result of decision step 85 is no, the method proceeds to decision step 86 where it is determined whether the switch 14 is turned off. If the result of decision step 86 is yes, the method proceeds to step 87 where the handheld sanitizer 10 ends delivery of energy. The method proceeds to step 88 where the method ends. If the result of decision step 85 is yes, the method proceeds to step 87. If the result of decision step 86 is no, the method proceeds to step 84.

In one embodiment of the present invention, the handheld sanitizer 10 additionally includes a display 27, as shown in dotted lines in FIG. 1. As shown 8 in FIG. 9, the display 27 serves as a user interface that shows selectable items to control operation of the handheld sanitizer 10. In one embodiment of the present invention, the selector 16 includes a series of up, down, right, left arrow buttons 92 that control placement of a cursor or other selection indication on the display 27. The selector 16 also includes a select button 94 to, when depressed, select the particular option highlighted by the cursor. As an example, the display 27 displays items Object and Energy as items for possible selection. The item Object can be selected when the handheld sanitizer 10 is to direct energy to a particular identified object or pathogen. The item Energy can be selected when a user of the handheld sanitizer 10 prefers to apply a certain type or level of energy. It will be appreciated that the selector 16 can be designed in myriad other manners, such as different input and selection means, to allow a user of the handheld sanitizer 10 to view and select options displayed on the display 27. Also other items, other than Object and Energy, can be displayed for selection. When an items is selected, any sub-items of the selected item are then displayed for further selection. When a sub-item is selected, any sub-items of the selected sub-item are then displayed for further selection. The drill down process repeats until the user finally selects the desired item or sub-item.

Figure 9:
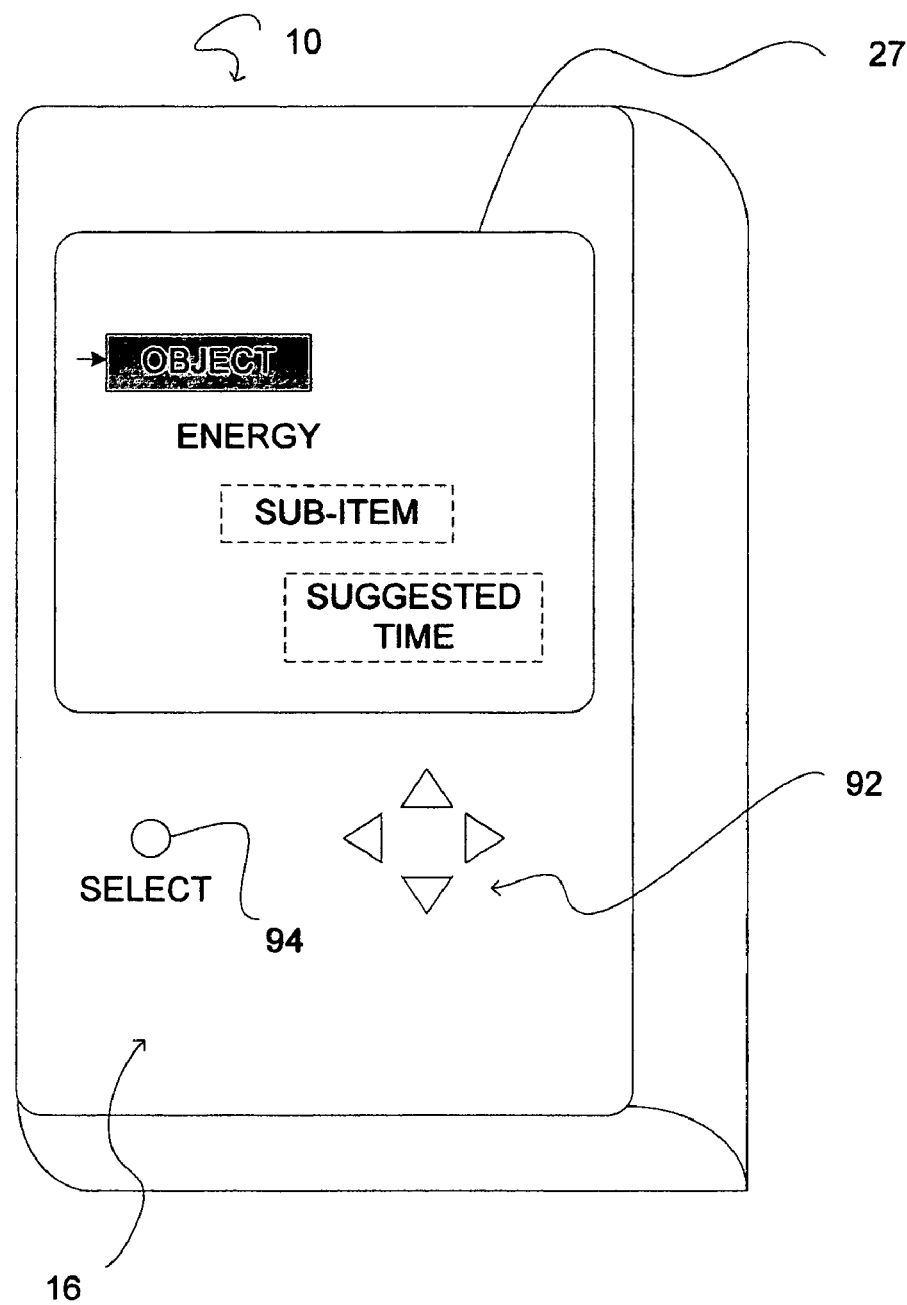
FIG. 9 shows a display and a selector of the handheld sanitizer in accordance with one of many embodiments of the present invention.
Figure 10:
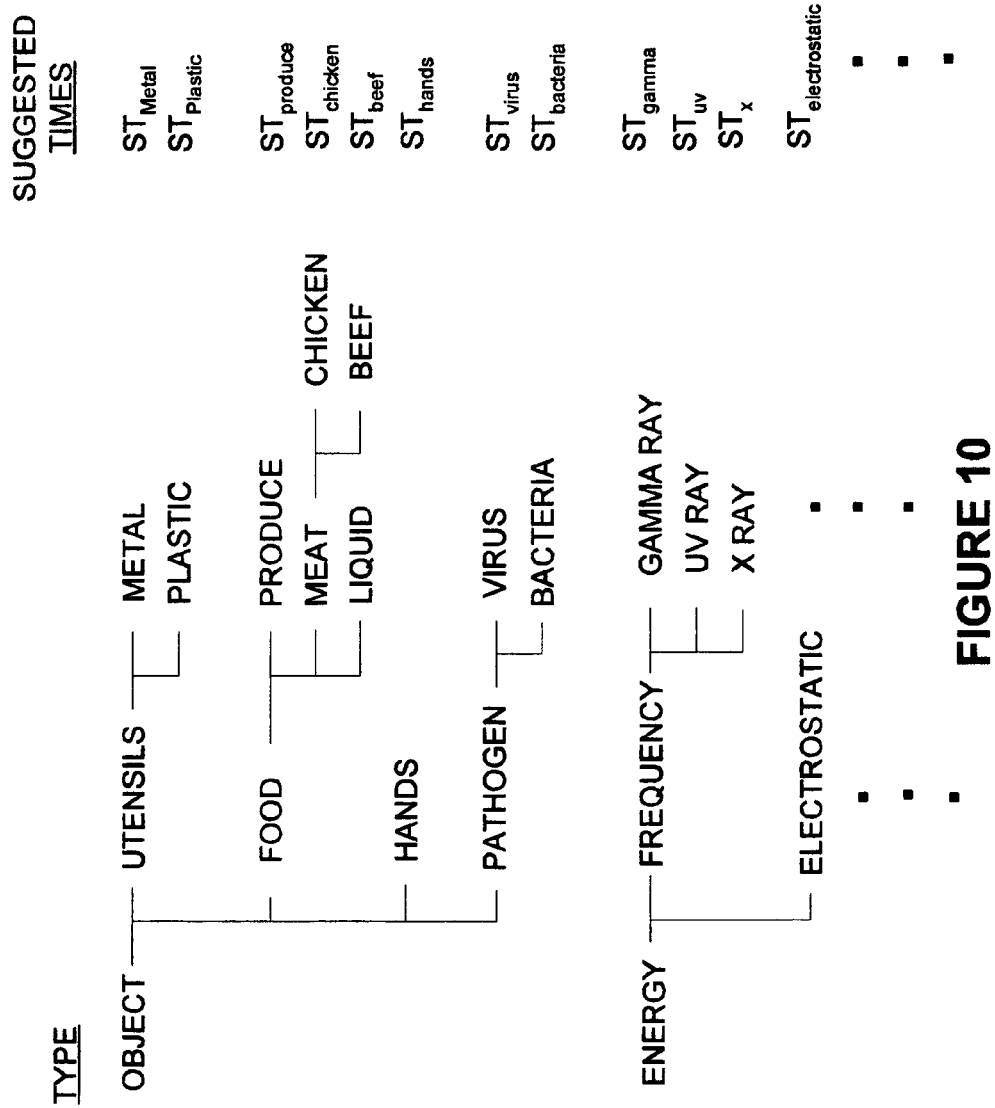
FIG. 10 shows a table including an item hierarchy with suggested times in accordance with one of many embodiments of the present invention.

FIG. 10 is a logical diagram of the hierarchical components of the item types Object and Energy. The item Object includes sub-items Utensils, Food, Hands, and Pathogen. The sub-item Utensils includes sub-items Metal and Plastic. The sub-item Food includes the sub-items Produce, Meat, and Liquid. The sub-item Meat includes sub-items Chicken and Beef. In this example, the item Hands does not have sub-items. The sub-item Pathogen includes sub-items Virus and Bacteria. The item Energy includes sub-items Frequency and Electrostatic. The sub-item Frequency includes sub-items Gamma-ray, UV, and X-ray. In this example, item Electrostatic does not have sub-items. It will be appreciated that the items and sub-items shown in FIG. 9 are exemplary only and that the present invention also contemplates more and fewer items and sub-items, and different hierarchical levels of items and sub-items. For example, in accordance with one embodiment of the present invention, the item Energy could additionally or alternatively include the sub-items Amplitude or Power, where the amplitude or power of a given energy form is used as another classification of a kind of energy for emission.

Each item or sub-item at the most granular level, or at the end of the hierarchical line, has an associated suggested time ST. The suggested time for each item or sub-item represents a recommended duration for application of energy by the handheld sanitizer 10 with respect to the particular item or sub-item to be cleansed. The suggested time can be formulated by various considerations including but not limited to optimizing degradation of pathogens, avoiding degradation of the particular Object item or sub-item, maximizing the difference between the maximum time and the suggested time to preserve safety, recognizing the inherent risk associated with the particular Energy item, and accounting for side and reactive effects of the item when energized. The suggested times ST can be stored in the controller 24. Upon selection of a particular option, the associated suggested time ST is displayed for selection. The suggested time ST can be selected by a user. Alternatively, the user can modify the suggested time ST using the selector 16 and then select the modification, as described in more detail below. In one embodiment of the present invention, the suggested time ST is pre-programmed into the handheld sanitizer 10. In one embodiment of the present invention, the suggested time ST is stored in the memory 27.

Figure 11:
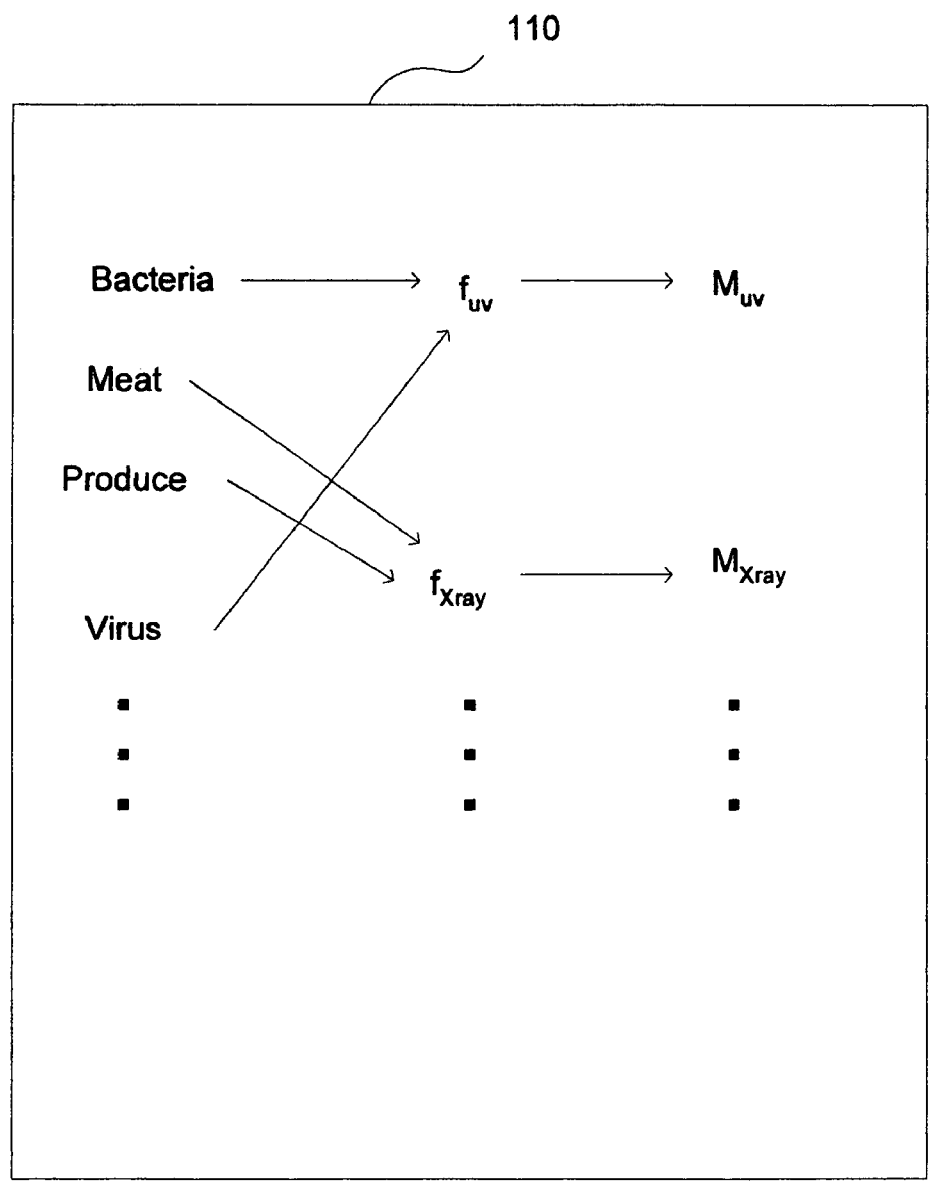
FIG. 11 shows a table associating items, energy levels, and maximum times in accordance with one of many embodiments of the present invention.

FIG. 11 is a table 110 of maximum times M and associated items and energy levels. The table 110 an be additionally or alternatively stored or programmed in the controller 24 or the memory 27. The maximum time M represents the maximum amount of time that energy of a particular kind can be safely applied by the handheld sanitizer 10. Determination of maximum time M is informed at least in part by scientific data and other sources of information regarding acceptable levels for each kind of energy to maintain health and safety. Table 110 associates selectable items to be energized by the handheld sanitizer 10 with a corresponding frequency f, or level, that represents an optimized application of energy by the handheld sanitizer 10 to cleanse the item or neutralize pathogens or other dangers thereof. The corresponding frequency in turn is associated with a maximum time of safe application of energy at that frequency. For example, if a user selects Bacteria as an item to be neutralized, UV energy is associated with Bacteria as an optimal energy level to neutralize bacteria. The UV energy is associated with a maximum time Muv that represents the longest amount of time that the UV energy should be applied. The maximum time Muv is determined by considerations of human safety primarily, and perhaps other factors such as preserving the safety and integrity of surrounding entities. As another example, the item Meat, optimally treated with x-ray energy, should be energized by x-ray energy no longer than the maximum time Mx. As yet another example, the user may instead choose a setting corresponding to desired application of a particular kind of energy, for example, UV energy, rather than an object or target to be energized. In this instance, the table 110 provides a maximum time Muv with the desired application of UV energy. When a particular maximum time M is reached during application of the handheld sanitizer 10, the controller 24 automatically provides a command to the power supply 26 or other components of the handheld sanitizer 10 to end application of energy.

Figure 12:
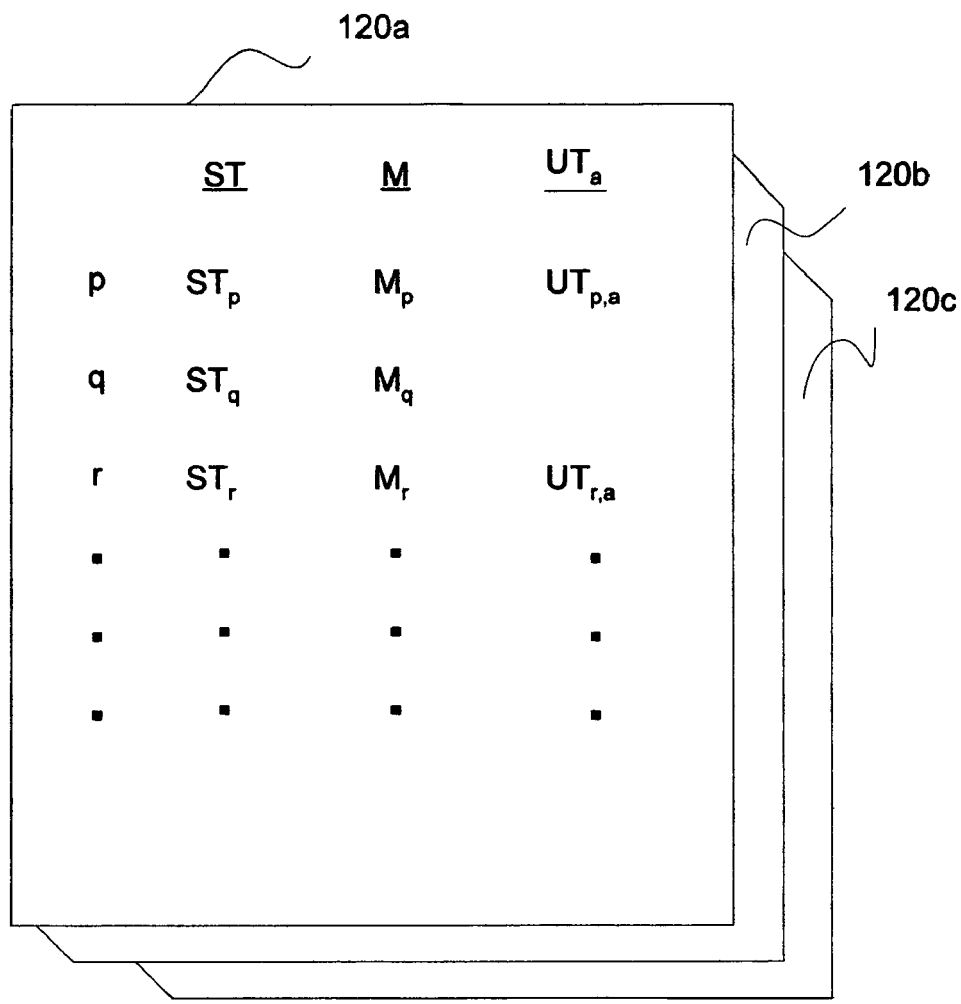
FIG. 12 shows a series of tables listing stored user-programmed times for various users in accordance with one of many embodiments of the present invention.

Upon display of suggested time ST, as discussed above, a user can modify the suggested time ST by, for example, depressing the select button and then entering a user-programmed time UT. The user time UT can be saved by, for example, further depression of the select button. It will be appreciated that the selector 16 can be designed in various ways in accordance with the present invention to allow user programming and creation of settings to control operation of the handheld sanitizer 10. The user time UT represents an alternative to the suggested time ST to accommodate the special preferences or concerns of the user. For example, the user may have safety or other concerns about energy applied by the handheld sanitizer 10, motivating the user to program user times UT that are smaller in magnitude than suggested times ST. As another example, because opinions about energy safety will likely continue to change over time, the handheld sanitizer 10 allows the user to program user times UT to reflect changing attitudes about energy safety. FIG. 12 illustrates a table 120a with columns corresponding to suggested times ST, maximum times M, and user times UTa. User times UTa include a column of values programmed by one of multiple users of the handheld sanitizer 10. Three exemplary rows correspond to a list of exemplary selectable items p, q, and r for illustration purposes only. For example, one selectable item p is associated with suggested time STp and maximum time Mp. For selectable item p, the user has programmed and saved a customized user time UTp,a. As seen in table 120, the user has not programmed or saved a customized user time associated with a selectable q and associated suggested time STq and maximum time Mq. It will be appreciated that the inclusion of suggested times STp, STq, STr, maximum times Mp, Mq, Mr, and user times UTq,a and UTr,a when programmed for selectable items p, q, and r, respectively, are illustrative. Selectable items p, q, and r, could correspond to, for example, Virus, Meat, and UV energy. Table 120a could of course includes other selectable items in any number with associated suggested times, maximum times, and user times when programmed by the user.

In one embodiment of the present invention, the handheld sanitizer 10 contemplates more than one user. The handheld sanitizer 10 is configured to provide instructions to and receive programming from multiple users. The information provided to users through the display 27 can guides and prompt the users to identify themselves, and appropriately program the handheld sanitizer 10 using the selector 16 in accordance with their particular needs and preferences. It will be appreciated that the prompts for and receipt of this programming can be implemented in various ways. The table 120a lists user times of a certain user of the handheld sanitizer 10. Table 120b, table 120c, and other possible tables store the programming of settings by additional users of the handheld sanitizer 10. For example, the programmed user times UT of a second user are listed in table 120b and the programmed user times UT of a third user are listed in table 120c. The accommodation of programming from multiple users of the handheld sanitizer 10 provides significant advantages with respect to versatility and economy. The tables 120a,b,c can be stored in the controller 24 or the memory 27. The values of maximum times M and suggested times ST in tables 120a,b,c are independent of the particular user of the handheld sanitizer 10 in one embodiment of the present invention.

Figure 13:
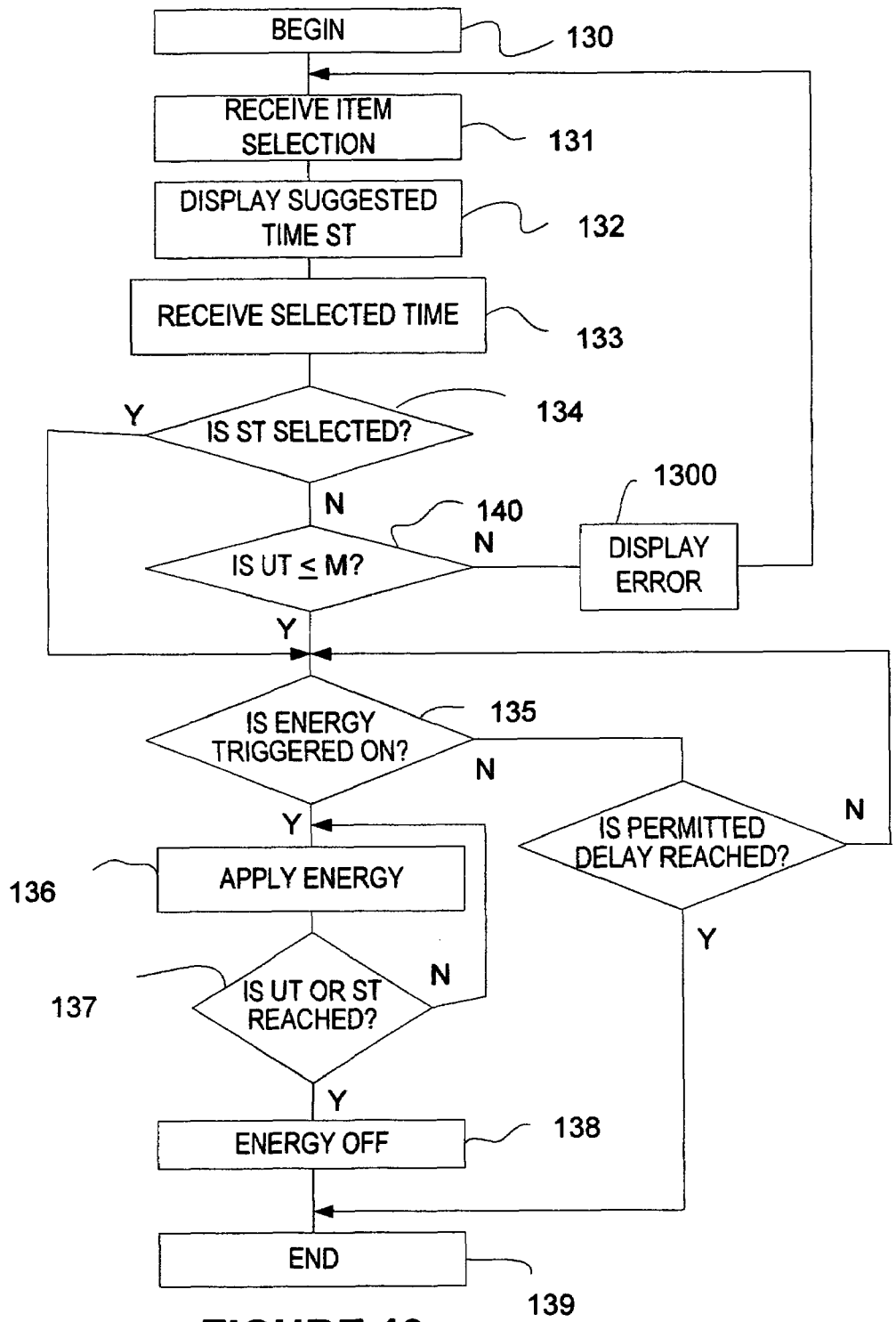
FIG. 13 shows a flow diagram of a method under a first operational mode constraining user-programmed times.

FIG. 13 is a method of allowing user programming in an operational mode where the maximum time M constrains acceptance of the user time UT in accordance with the present invention. The method begins at step 130 and proceeds to step 131 where the handheld sanitizer 10 receives program settings regarding, for example, selection of an item that represents desired application of certain energy or an object to be energized. The method proceeds to step 132 where a suggested time ST is displayed to a user. The method proceeds to step 133 where the handheld sanitizer 10 receives a time selected by the user. The method proceeds to decision step 134 where it is determined whether the suggested time ST has been selected by the user. If the result is yes, the method proceeds to decision step 135 where it is determined whether the user has engaged the trigger to begin delivery of energy. If the result is yes, the method proceeds to step 136 where the handheld sanitizer 10 delivers energy. The method proceeds to decision step 137 where it is determined whether the suggested time ST or user time UT, whichever has been selected, has elapsed. If the result is yes, the delivery of energy by the handheld sanitizer 10 is turned off, and the method proceeds to step 139 where the method ends. If the result of decision step 134 is no, the method proceeds to decision step 140 where it is determined whether the programmed user time UT is less than or equal to a maximum time M corresponding to the selected item. If the result is no, the method proceeds to step 1300 where an error message is displayed to the user. In this operational mode, the handheld sanitizer 10 cannot be programmed to deliver energy for a time longer than the maximum time M. From step 1300, the method proceeds to step 131. If the result of decision step 140 is yes, the method proceeds to decision step 135. If the result of decision step 135 is no, the method proceeds to decision step 1301 where it is determined whether a permitted amount of delay allowing the user to trigger delivery of energy has elapsed. If the result of decision step 1301 is yes, the time elapsed exceeded the permitted amount, and the method proceeds to step 139. If the result of decision step 1301 is no, the method proceeds to decision step 135. If the result of decision step 137 is no, the method proceeds to step 136.

Figure 14:
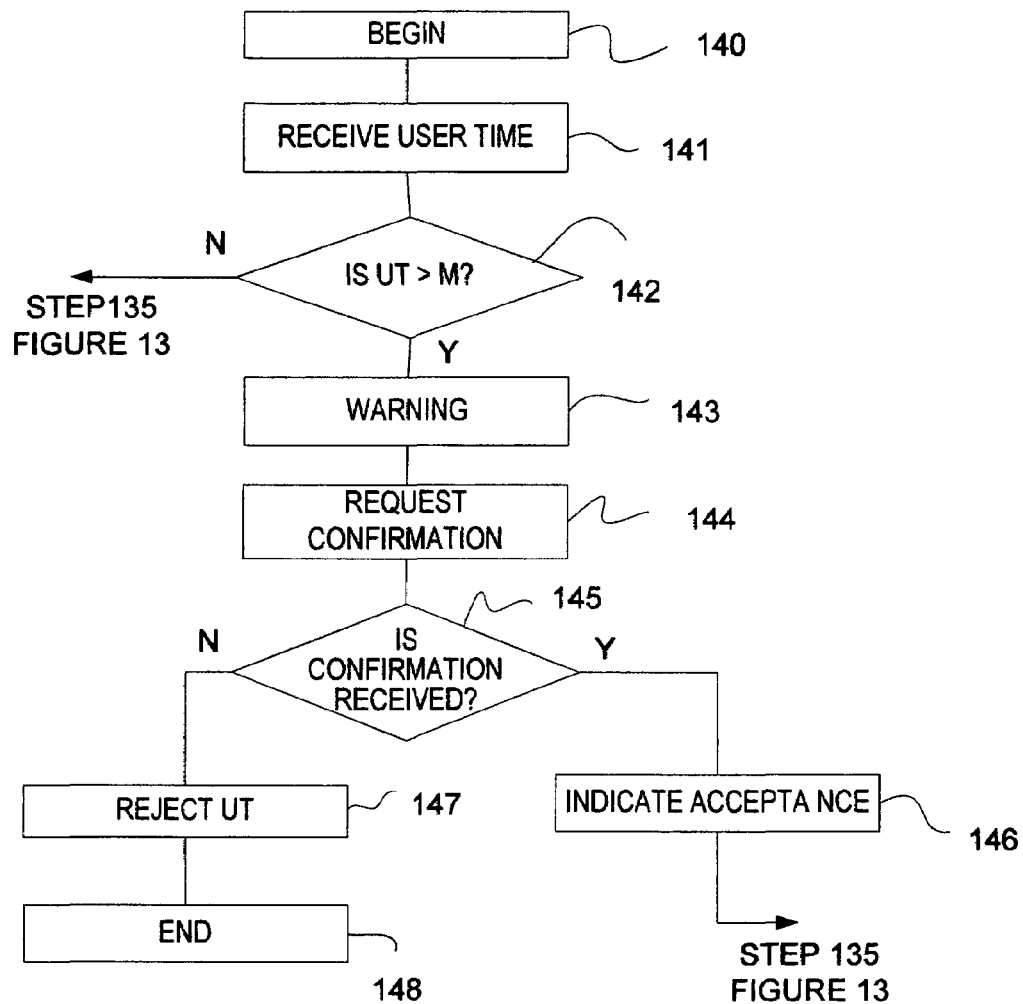
FIG. 14 shows a flow diagram of a method under a second operational mode allowing user-programmed times to exceed maximum times.

FIG. 14 is a method of allowing user programming in an operational mode where the maximum time M can be overridden in accordance with the present invention. The method begins at step 140 and proceeds to step 141 where the handheld sanitizer 10 receives a user time UT for a previously selected item. The method proceeds to decision step 142 where it is determined whether the user time UT is greater than a maximum time M. If the result is yes, the method proceeds to step 143 where the user is warned that the programming provided by the user exceeds the maximum time M. The method proceeds to step 144 where the handheld sanitizer 10 requests confirmation from the user that the user time UT is desired. The request for confirmation is a feature motivated in part by balance of safety considerations and user freedom. The method proceeds to decision step 145 where it is determined whether the requested confirmation has been provided by the user. If the result is yes, the method proceeds to step 146 where the handheld sanitizer 10 indicates acceptance of the user time UT, and the method proceeds to appropriately deliver energy as in, for example, step 135 (FIG. 13). If the result of decision block 142 is no, the method proceeds to appropriately deliver energy as in, for example, step 135 (FIG. 13). If the result of decision step 145 is no, the method proceeds to step 147 where the user time UT is rejected by the handheld sanitizer 10, and the method proceeds to step 148 where the method ends.

All of the many methods and techniques discussed or implied herein can be in whole or in part performed by suitably designed software. The software can be stored in a memory of the handheld sanitizer 10. The software can also be stored on a computer readable medium, such as a disk or other optical medium. In one embodiment, the software, stored on a medium, can be installed on the computing device and then transferred in part of whole to the handheld sanitizer 10. Alternatively, the software could be downloaded over a network or from the Internet and then stored in the computing device.

While the preferred embodiments, and alternative embodiments, have been variously illustrated and described, it will be appreciated that various changes can be made therein without departing from the spirit and scope of the invention. For example, FIGS. 11 and 12 illustrate tables listing various values. It will be appreciated that other and additional values can be listed on other and additional tables that are organized differently. Alternatively, the values can be stored in the handheld sanitizer 10 by means other than tables and to components other than the controller 24 and the memory 27.

As another example, the selector 16 has been described as allowing selection of settings through buttons. It will be appreciated that the selector 16 can be of any design that permits user input. For example, control knobs or other mechanical or electromechanical devices that allow user input to perform programming are within contemplation of the present invention. As another example, the selector could be an alphanumeric or other keypad of selectable characters and numbers and other keys appropriate to receive user inputs. The selector can alternatively be a touch screen or other user interface capable of receiving inputs by the user.

It also will be appreciated that the types of energy describe are illustrative only. As science and research develops, additional forms of energy may prove effective in neutralizing or destroying pathogens and other environmental dangers. The present invention includes these additional types of energy for delivery by the handheld sanitizer 10.

The FIG. 1 depicts one of many possible embodiments of the handheld sanitizer 10. In other embodiments, the handheld sanitizer 10 can be dimensioned and designed differently as long as the total size and shape of the handheld sanitizer 10 is suitable for convenient portability and manual use by the hands of users.

Figure 15:
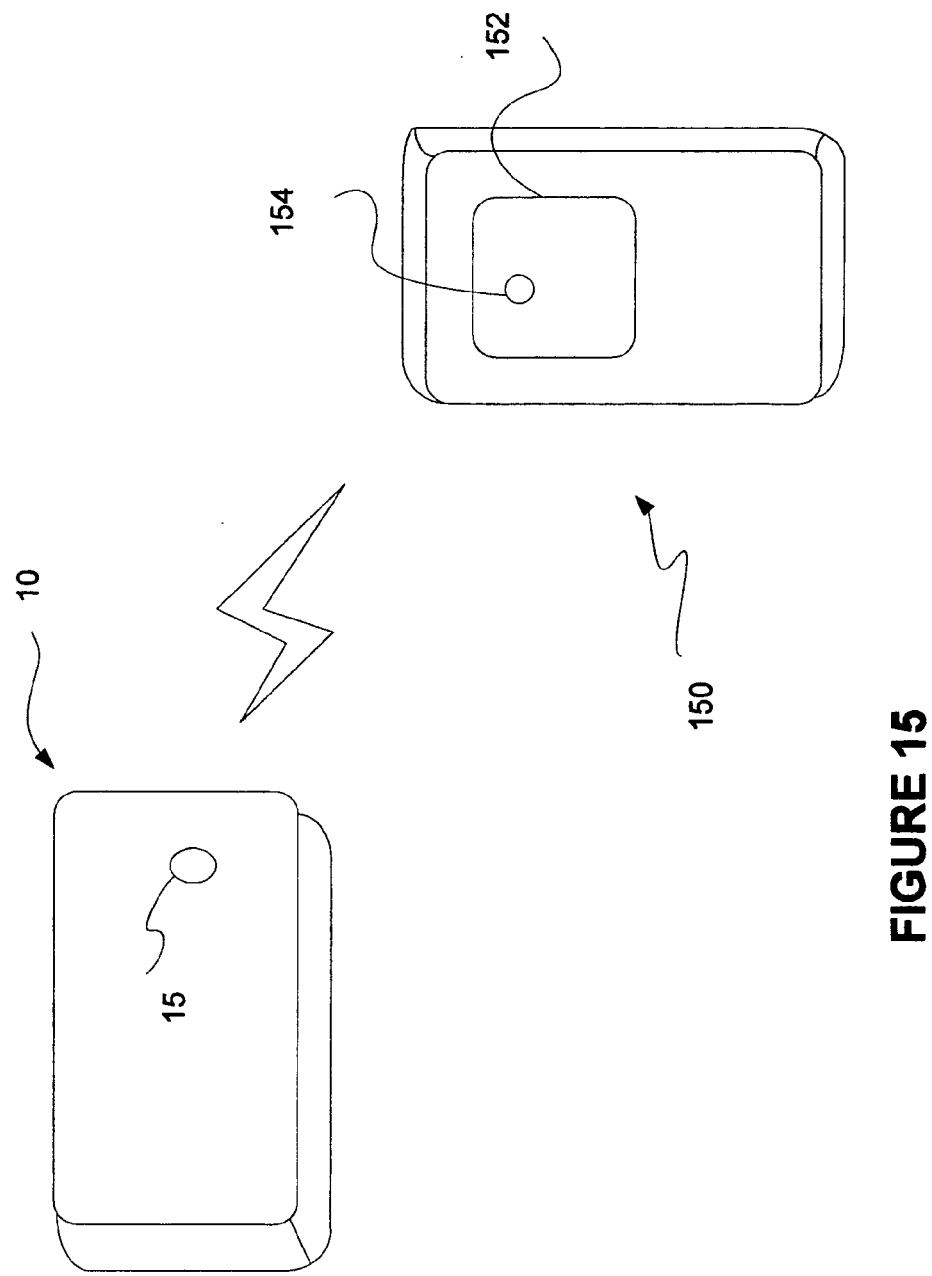
FIG. 15 shows a remote controller for controlling the handheld sanitizer in accordance with one of many embodiments of the present invention.

As an example of another embodiment of the present invention, the handheld sanitizer 10 includes a receiver 11 (FIG. 2) exposed to the surface of the handheld sanitizer 10 through a remote control interface 15 (FIG. 1). Through the interface 15, the receiver 11 is designed to receive remote control commands and provide those commands to the controller 24. The interface 15 could be located in many locations on the handheld sanitizer 10. The remote control commands originate from a remote controller 150 as shown in FIG. 15. In one embodiment of the present invention, the remote controller 150 includes a command pad 152, having an on/off button 154, and conventional components to generate infrared or other signals to allow a user of the remote controller 150 to remotely turn on and turn off the handheld sanitizer 10. In operation, a user of the handheld sanitizer 10 can directly and manually program the handheld sanitizer 10 to a desired setting, as discussed above. Thereafter, the user might choose to venture away from the handheld sanitizer 10 and leave the handheld sanitizer 10 near an object to be sanitized. The user might choose to venture away to create a distance in the interest of safety between the user and the energy emitted by the handheld sanitizer 10. To remotely initiate the emission of energy by the handheld sanitizer 10, the user could command the remote controller 150 to turn on the handheld sanitizer 10 by engaging the on/off button 154 and directing energy at the object to be sanitized while the user is a safe distance away. In one embodiment of the present invention, the command pad 152 includes an alphanumeric key pad for allowing more commands from the remote controller 150 and thus more remote control of the handheld sanitizer 10.

As example of another embodiment of the present invention, the handheld sanitizer 10 includes a safety feature that controls who is permitted to use the handheld sanitizer 10. The handheld sanitizer 10 stores in the memory 25 a password, ID, or other authentication information concerning a user or owner of the handheld sanitizer 10 before the handheld sanitizer 10 can be operated. The authentication information can be programmed by the manufacturer. Alternatively, a user or owner of the handheld sanitizer 10 can program (and re-program) the authentication information using an alphanumeric or other keyboard, touch screen, or other kind of input device serving as the selector 16. Before intended operation of the handheld sanitizer 10, the user is required to provide the correct authentication information as stored in the handheld sanitizer 10, or else the handheld sanitizer 10 will not operate. The required provision of authetication information in one embodiment helps to ensure usage by only authorized persons or users and reduces the risk that the handheld sanitizer 10 will be misappropriated or abused by unauthorized persons who might employ the handheld sanitizer 10 for unintended or dangerous purposes.

Figure 16:
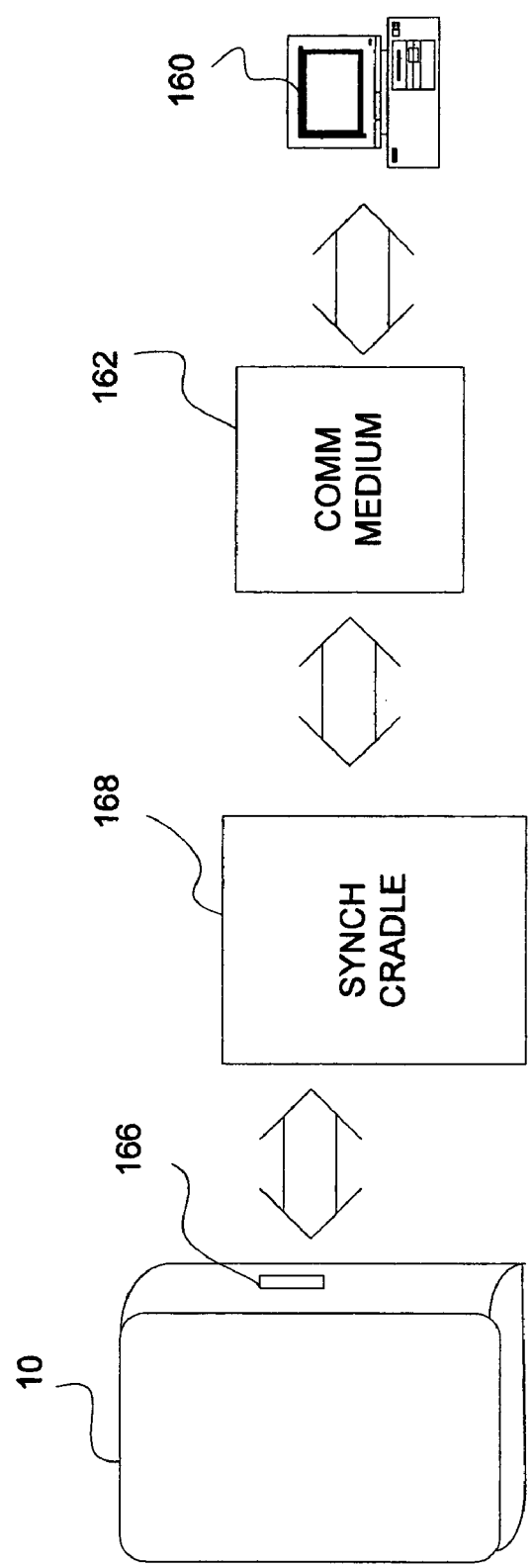
FIG. 16 shows a synchronization system in accordance with one of many embodiments of the present invention.

FIG. 16 illustrates a logical block diagram of a synchronization system involving one embodiment of the handheld sanitizer 10 that includes a port 166. Through the port 166 the handheld sanitizer 10 is capable of synchronizing and communicating with another computing device 160 via a communications medium 162. The communications medium 162 could be a IEEE 1394 (Firewire) or other conventional wire or wireless connection with appropriate conventional porting such as USB or other type. The computer device 160 is able to access, receive, download, and store current and preferred data reflecting the latest scientific information and thinking about optimal conditions and methods to control the handheld sanitizer 10 in successfully targeting pathogens. The computing device 160 under control of installed software, perhaps provided on a computer readable medium, can download from the Internet or other data source, or otherwise receive and contain, the latest data relating to the operation or control of the handheld sanitizer 10, including but not limited to information related to maximum times M, suggested times ST, and user times UT. For example, in the future the scientific community may agree that the application of a certain type of energy to kill a certain pathogen should last for a duration longer than previously thought. Communications between the handheld sanitizer 10 and the computing device 160 allows transfer of such data stored in the computing device 160 to the handheld sanitizer 10. Such communications also allow the transfer of data stored in the handheld sanitizer 10 to the computing device 160 to create a copy of such information for archival, analysis, or other purposes better served with the help of the computing device 160. In one embodiment, the communications and synchronization capabilities of the handheld sanitizer 10, and the downloading of information by the computer device 160 can be performed by installed software from a computer readable medium running on the computing device 160. In one embodiment of the present invention, the handheld sanitizer 10 is communicatively connected to the communications medium 162 through a synchronization cradle 168. The synchronization cradle 168 can be configured to allow physical contact with the handheld sanitizer 10. Data from the handheld sanitizer 10 is provided to the synchronization cradle 168 and then passed to the computing device 160 over the communications medium 162. In another embodiment of the present invention, the handheld sanitizer 10 can be used with other safety apparatus. For example, a user of the handheld sanitizer 10 or someone nearby can wear gloves, a mask, an apron-like cover, or other clothing designed to protect the user from the energy emitted by the handheld sanitizer 10. As another example, a user of the handheld sanitizer 10 or someone nearby could wear protective eyewear or other coverings to safeguard the eyes and other body parts.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. As one example, a system in accordance with the present invention described or illustrated herein equally discloses the corresponding methods in accordance with the present invention, and vice versa. Thus, the present invention is not intended to be limited to the embodiments shown herein but is to be accorded the widest scope consistent with the principles and novel features disclosed herein. Within the scope of the appended claims, it will be appreciated that the present invention can be practiced in various manners otherwise than as specifically described herein.

We claim:

1. A system for degrading pathogens comprising:
a selector for receiving inputs of a user, said inputs including a user programmed time UT representing a duration, provided by the user, during which an energy generator and a director produce and emit energy;

an energy generator for producing energy to neutralize environmental danger;

a controller, communicatively coupled with the selector, for controlling operation of the energy generator based on the inputs;

a memory, communicatively coupled to the selector, for storing programmed information including the user programmed time UT; and a case, containing the energy generator and the controller, dimensioned to fit in a hand of the user, the selector located on an outer surface of the case.

2. The system of claim 1 further comprising a director, communicatively coupled to the energy generator, for emitting energy produced by the energy generator.

3. The system of claim 2 wherein the energy generator and the director produce and emit energy for a duration not longer than a maximum time M representing a preprogrammed duration of time after which the energy generator and director stop production and emission of energy the maximum time M different from the user programmed time UT, the memory storing the maximum time M.

4. The system of claim 1 further comprising a display, located on an outer surface of the case, that shows items selectable by the user through appropriate manipulation of the selector.

5. The system of claim 4 wherein the display shows a suggested time ST representing a recommended duration during which the energy generator and the director produce and emit energy, the memory storing the suggested time ST.

6. The system of claim 1 wherein the memory stores authentication information, the user required to provide the authentication information before energy is produced by the energy generator.

7. The system of claim 1 wherein the memory stores user programmed times UT provided by a plurality of users, each of the user programmed times UT representing a duration, determined by one of the plurality of users, during which the energy generator and the director produce and emit energy.

8. The system of claim 1 wherein the energy produced by the energy generator is electrostatic energy.

9. The system of claim 1 wherein the energy produced by the energy generator is electromagnetic wave energy.

10. A portable handheld sanitization device comprising:

a selector for receiving inputs of a user;

an energy generator for producing energy to reduce environmental pathogens;

a controller, communicatively linked with the selector, for controlling operation of the energy generator based on the inputs;

a director, communicatively linked with the energy generator, for emitting energy produced by the energy generator at the environmental pathogens;

a memory, communicatively coupled to the selector, for storing both information programmed by the user and information preprogrammed by a non-user, said programmed information and preprogrammed information concerning the duration during which the energy generator and the director produce and emit energy; and a display, communicatively linked to the selector and the controller, for showing items selectable by the user through appropriate manipulation of the selector.

11. The device of claim 10 further where the memory stores a time selected from the group consisting of a maximum time M, representing a preprogrammed duration of time after which the energy generator and director stop production and emission of energy, a suggested time ST, representing a recommended duration during which the energy generator and the director produce and emit energy, a user programmed time UT, representing a duration, provided by the user, during which the energy generator and the director produce and emit energy, the controller effecting shut down of the energy generator and the director after lapse of the time.

12. The device of claim 11 wherein the maximum time M, the suggested time ST, and the user programmed time UT are directly or indirectly associated with a particular type of energy to be emitted by the director.

13. The device of claim 10 wherein the memory stores user programmed times UT provided by a plurality of users, each of the user programmed times UT representing a duration, determined by one of the plurality of users, during which the energy generator and the director produce and emit energy.

14. The device of claim 10 wherein the selectable items shown by the display relate to types of objects or pathogens to be energized.

15. The device of claim 10 wherein the selectable items shown by the display relate to types of energy to be emitted.

16. The device of claim 10 further comprising a receiver, coupled to the controller, for receiving remote control commands.

17. The device of claim 10 further comprising a communications port, coupled to the controller and memory, for allowing communications with another computing device.

18. The device of claim 17 where said communications port facilitates transfer of data with the other computing device regarding said programmed and preprogrammed information.

19. A portable device dimensioned to be handheld comprising:

an energy generator for generating energy to degrade environmental pathogens;

a director, communicatively linked to the energy generator, for emitting the generated energy; and a controller, communicatively coupled with the director and energy generator, for allowing the energy generator and the director to generate and emit energy for a predetermined time and for effecting shut down of the generation and emission of energy upon lapse of the predetermined time;

a memory, communicatively linked with the selector, for storing a suggested time ST, representing a recommended duration during which the energy generator and the director produce and emit energy, for a particular item; and a selector, communicatively coupled to the controller, for receiving a user programmed time UT, representing a duration, provided by a user, during which the energy generator and the director produce and emit energy for the particular item, the controller effecting shut down of energy after lapse of the user programmed time UT after a user rejects the suggested time ST for the particular item.

20. The device of claim 19 wherein the memory stores a maximum time M, representing a preprogrammed duration of time after which the energy generator and director stop production and emission of energy for the particular item, the controller effecting shut down of energy after lapse of the user programmed time UT instead of the maximum time M when desired by the user.

* * * * *